United States Patent
Coffey et al.

(10) Patent No.: US 7,256,217 B2
(45) Date of Patent: Aug. 14, 2007

(54) PRODRUGS OF EXCITATORY AMINO ACIDS

(75) Inventors: David Scott Coffey, Indianapolis, IN (US); James Allen Monn, Indianapolis, IN (US); Concepcion Pedregal-Tercero, Madrid (ES); Steven Wayne Pedersen, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 529 days.

(21) Appl. No.: 10/250,448

(22) PCT Filed: Dec. 14, 2001

(86) PCT No.: PCT/US01/45866

§ 371 (c)(1),
(2), (4) Date: Nov. 12, 2003

(87) PCT Pub. No.: WO02/055481

PCT Pub. Date: Jul. 18, 2002

(65) Prior Publication Data

US 2004/0121962 A1    Jun. 24, 2004

Related U.S. Application Data

(60) Provisional application No. 60/329,786, filed on Oct. 16, 2001.

(30) Foreign Application Priority Data

| Jan. 11, 2001 | (EP) | .................................. 01500007 |
| Aug. 2, 2001 | (EP) | .................................. 01500206 |
| Nov. 7, 2001 | (EP) | .................................. 01500263 |

(51) Int. Cl.
*A61K 31/16* (2006.01)
*C07C 233/23* (2006.01)

(52) U.S. Cl. ...................... 514/619; 564/193
(58) Field of Classification Search ................ 564/123, 564/193; 514/619
See application file for complete search history.

(56) References Cited

U.S. PATENT DOCUMENTS

| 5,661,184 | A |   | 8/1997 | Helton et al. |
| 5,726,320 | A |   | 3/1998 | Robey |
| 5,750,566 | A | * | 5/1998 | Monn et al. ................ 514/510 |
| 5,882,671 | A |   | 3/1999 | Helton et al. |
| 5,925,680 | A |   | 7/1999 | Helton et al. |
| 5,925,782 | A |   | 7/1999 | Monn |

FOREIGN PATENT DOCUMENTS

| EP | 0 696 577 A | 2/1996 |
| EP | 1 052 246 A | 11/2000 |
| US | PCT/US02/36145 | 5/2002 |
| WO | WO 00 04010 A | 1/2000 |
| WO | WO 02 22627 A | 3/2002 |
| WO | WO 02/055485 A1 | 7/2002 |
| WO | WO 03/006489 A2 | 1/2003 |
| WO | WO 03/045898 A1 | 6/2003 |

OTHER PUBLICATIONS

C. Y. Yang et al., Intestinal peptide transport systems and oral drug availability, *Pharm. Res.* 1999, 16(9), 1331-1343.
V. Ganapathy et al., Intestinal transport of amino acids and peptides, *Physiology of the gastrointestinal tract*, L. R. Johnson, Editor. 1994, Raven Press: New York, pp. 1773-1794.
D. M. Mathews et al., Peptide absorption, *Gastroenterology* 1976, 71, 151-161.
K. Inui, M. et al., Transepithelial transport of oral cephalosporins by monolayers of intestinal epithelial cell line Caco-2: Specific transport systems in apical and basolateral membranes, *J. Pharmacol. Exp. Ther*, 1992, 261(1), 195-201.
Kim, J. S. et al., Absorption of ACE inhibitors from small intestine and colon, *J. Pharm. Sci.* 1994, 83(9), 1350-1356.
Hashimoto, N. et al., Renin inhibitor: transport mechanism in rat small intestinal brush-border membrane vesicles, *Pharm. Res.* 1994, 11(10), 1448-1451.
Döring, F. et al., Minimal molecular determinants of substrates for recognition by the intestinal peptide transporter, *J. Biol. Chem.* 1998, 273, 23211-23218.
Han, H. K. et al., 5'-Amino acid esters of antiviral nucleosides, acyclovir, and AZT are absorbed by the intestinal PEPT1 peptide transporter, *Pharm. Res.* 1998, 15, 1154-1159.
Hu, M. et al, Use of peptide carrier system to improve the intestinal absorption of L-alpha-methyldopa: carrier kinetics, intestinal permeabilities and in vitro hydrolysis of dipeptidyl derivatives of L-alpha-methyldopa. *Pharm. Res.* 1989, 6, 66-70.

(Continued)

*Primary Examiner*—Kamal A. Saeed
*Assistant Examiner*—Janet L. Coppins
(74) *Attorney, Agent, or Firm*—Danica Hostettler; Arvie J. Anderson

(57) ABSTRACT

This invention relates to synthetic excitatory amino acid prodrugs according to formula (I) and processes for their preparation. The invention further relates to methods of using, and pharmaceutical compositions comprising, the compounds for the treatment of neurological disorders and psychiatric disorders (I)

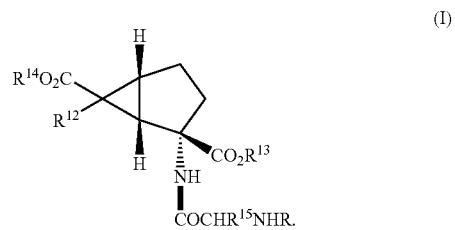

5 Claims, No Drawings

OTHER PUBLICATIONS

Bailey, P. D. et al., How to make drugs orally active: a substrate template for peptide transporter PepT1, *Angew. Chem. Int. Ed. Eng.* 2000, 39(3), 506-508.

Bai, Jane P. F. et al, Structural Specificity of Mucosal-Cell Transport and Metabolism of Peptide Drugs: Implication of Oral Peptide Drug Delivery., *Pharm. Res.*, 9 (8), 1992, 969-978.

Langguth P. et al., The challenge of proteolytic enzymes in intestinal peptide delivery., *Journal of Controlled Release*, 46, 1997, 39-57.

Walter E. et al., The intestinal peptide carrier: A potential transport system for small peptide derived drugs, *Adv. Drug Deliv. Rev.* 1996, 20, 33-58.

Amidon G. L. et al., Absorption of Peptide and Peptidomimetic drugs., *Annu. Rev. Pharmacol. Toxicol.*, 1994, 34, 321-341.

Bai, Jane P-F et al., Utilization of Peptide Carrier System To Improve Intestinal Absorption: Targeting Prolidase as a Prodrug-Converting Enzyme., *J. Pharm. Sci.*, 1992, 81 (2), 113-116.

Lee, Chao-Pin et al., Advanced Drug Delivery, 23, 1997, 47-62.

Pauletti, Giovanni M. et al., Advanced Drug Delivery Reviews, 1997, 27, 235-256.

Oliyai, Reza, Advanced Drug Delivery Reviews, 1996, 19, 275-286.

Steffansen, Bente et al., European Journal of Pharmaceutical Sciences, 1999, 8, 67-73.

Nielsen, Carsten Uhd et al., Journal of Controlled Release, 2001, 76, 129-138.

Steingrimsdottir, Hlif et al., Antimicrobial Agents and Chemotherapy, 2000, 44 (1), 207-9.

Anand, Banmeet S. et al., Current prodrug strategies via membrane transporters/receptors, Expert Opin. Biol. Ther., 2002, 2(6), 607-620.

Dantzig, Anne H., Oral absorption of $\beta$-lactams by intestinal peptide transport proteins, Advanced Drug Delivery Reviews, 1997, 63-76.

\* cited by examiner

PRODRUGS OF EXCITATORY AMINO ACIDS

This is the national phase application, under 35 USC 371, for PCT/US01/45866, filed Dec. 14, 2001, which claims the benefit of European Application No. 01500263.7, filed Nov. 7, 2001, U.S. Provisional Application No. 60/329,786 filed on Oct. 16, 2001, European Application No. 01500206.6 filed on Aug. 2, 2001 and European Application No. 01500007.8 filed on Jan. 11, 2001.

This invention relates to synthetic excitatory amino acid prodrugs (and their pharmaceutically acceptable salts) and processes for their preparation. The invention further relates to methods of using, and pharmaceutical compositions comprising, the compounds for the treatment of neurological disorders and psychiatric disorders.

Treatment of neurological or psychiatric disorders, such as anxiety disorder, have been linked to selective activation of metabotropic excitatory amino acid receptors such as (+)-2-aminobicyclo[3.1.0]hexane-2,6-dicarboxylic acid, also known as LY354740, which is disclosed in U.S. Pat. No. 5,750,566 (the '566 patent) issued May 12, 1998 is an active MGLUR2 receptor agonist, CNS Drug Reviews, 5, pgs. 1-12 (1999).

The present invention provides for a prodrug form of LY354740, which enhances the in vivo potency of LY354740, producing higher oral exposure of the parent compound. In addition, when compounds of the present invention are administered, no circulating level of prodrug was detected with high in vitro bioconversion to the parent molecule. Further, the peptide prodrugs are stable under all ranges of pH and are nontoxic. Compounds of the present invention represent the best approach for maintaining LY354740-like safety and efficacy in humans with increased oral bioavailability. Preclinical studies with, (1S,2S,5R,6S)-2-[(2'S)-(2'-Amino)-propionyl]amino-bicyclo[3.1.0]hexane-2,6-dicarboxylic acid hydrochloride, the compound of the present invention, has shown greatly enhanced oral potency in the treatment of anxiety without the attendant problems of toxicity, instability at desired pH ranges and low in vivo conversion.

Accordingly, the present invention provides a compound of formula I

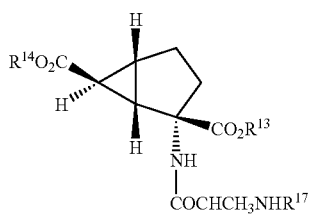

wherein $R^{13}$, $R^{14}$ and $R^{17}$ are hydrogen;

or a pharmaceutically acceptable salt thereof.

Compounds of the invention have been found to be useful prodrugs for LY354740 a selective agonist of metabotropic glutamate receptors and are therefore useful in the pharmaceutical treatment of diseases of the central nervous system such as neurological diseases, for example neurodegenerative diseases, and as antipsychotic, anxiolytic, drug-withdrawal, antidepressant, anticonvulsant, analgesic and antiemetic agents.

It will be appreciated that the compounds of formula (I) contain at least four asymmetric carbon atoms, three being in the cyclopropane ring and one being at the α-carbon of the amino acid group. Accordingly, the compounds of the invention may exist in and be isolated in enantiomerically pure form, in racemic form, or in a diastereoisomeric mixture.

The amino acid moiety preferably has the natural amino acid configuration, i.e. the L-configuration relative to D-glycerol aldehyde.

The present invention includes pharmaceutically acceptable salts of the compound of formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Some particular salts provide certain formulation advantages due to their crystalline form. Non-crystalline forms of compounds may be amorphous and hygroscopic. Crystalline forms of pharmaceutical compounds are sometimes more desirable because they are not amorphous.

A particular pharmaceutically acceptable salt of the peptide of formula I is (1S,2S,5R,6S)-2-[(2'S)-(2'-Amino)-propionyl]amino-bicyclo[3.1.0]hexane-2,6-dicarboxylic acid hydrochloride salt.

Another particular pharmaceutically acceptable salt of the peptide of formula I is (1S,2S,5R,6S)-2-[(2'S)-(2'-Amino)-propionyl]amino-bicyclo[3.1.0]hexane-2,6-dicarboxylic acid methane sulfonate salt.

Acids commonly employed to form such salts include inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, methane-sulfonic or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterization or purification.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorder such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable salt thereof.

The formula I compounds of the present invention treat a variety of other neurological disorders in patients that are associated with glutamate dysfunction, including muscular spasms, convulsions, migraine headaches, urinary incontinence, pain, premenstrual dysphoric disorder (PDD), psychosis, (such as schizophrenia), drug tolerance and withdrawal (such as nicotine, opiates and benzodiazepines), anxiety and related disorders, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable salt thereof.

A compound of Formula I may be made by a process which is analogous to one known in the chemical art for the production of structurally analogous heterocyclic compounds or by a novel process described herein. Such processes and intermediates useful for the manufacture of a compound of Formula I as defined above are provided as further features of the invention and are illustrated by the following procedures in which, unless otherwise specified, the meanings of the generic radicals are as defined above.

(A) For a compound of formula I in which $R^{13}$, $R^{14}$, and $R^{17}$ are hydrogen (a di-acid), deprotecting the amine group of a compound of formula I where $R^{17}$ is tert-butoxy carbonyl or a nitrogen protecting group, with an acid as described in the General Procedures for Examples 3 and 4.

(B) For a compound of formula I in which $R^{13}$ and $R^{14}$ are both hydrogen (a di-acid), deprotecting a compound of formula I where $R^{13}$ and $R^{14}$ are not both hydrogen as described in Scheme 2.

(C) For a compound of formula I in which $R^{13}$ and $R^{14}$ are not both hydrogen, amidating a compound of formula II

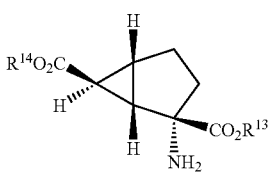

II with a corresponding amino acid of formula III.

HOOCCHCH$_3$NHR$^{17}$   III in which p is O or any integer from 1-10 and $R^{17}$ is tert-butoxy carbonyl or a nitrogen-protecting group as described in the General Procedure for Example 1.

(D) For a compound of formula II where $R^{13}$ and $R^{14}$ are not hydrogen, where $R^{13}$ and $R^{14}$ may be a carboxy-protecting ester group (a di-ester), esterifying a compound of formula II where $R^{13}$ and $R^{14}$ are both hydrogen (a di-acid).

(E) For a compound of formula II in which $R^{13}$ and $R^{14}$ are not both hydrogen (a di-ester), deprotecting a compound of formula IV

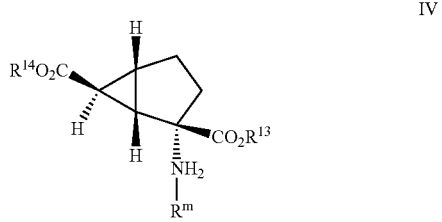

IV where $R^m$ is a nitrogen protecting group, as described in Preparation 2.

(F) For a compound of formula II where $R^{13}$ and $R^{14}$ are not both hydrogen (a di-ester), esterifying a compound of formula IV, as described in Preparation 2.

(G) For a compound of formula IV where $R^{13}$ and $R^{14}$ are both hydrogen (a di-acid), protecting the amine group of a compound of formula II as described in Preparation 1.

The term "nitrogen protecting group," as used herein, refers to those groups intended to protect or block the nitrogen group against undesirable reactions during synthetic procedures. Choice of the suitable nitrogen protecting group used will depend upon the conditions that will be employed in subsequent reaction steps wherein protection is required, as is well within the knowledge of one of ordinary skill in the art. Commonly used nitrogen protecting groups are disclosed in T. W. Greene and P. G. M. Wuts, Protective Groups In Organic Synthesis, 2$^{nd}$ Ed. (John Wiley & Sons, New York (1991)).

The term "carboxy-protecting group" as used herein refers to one of the ester derivatives of the carboxylic acid group commonly employed to block or protect the carboxylic acid group while reactions are carried out on other functional groups of the compound. Particular values include, for example, methyl, ethyl, tert-butyl, benzyl, methoxymethyl, trimethylsilyl, and the like. Further examples of such groups may be found in T. W. Greene and P. G. M. Wuts, Protecting Groups in Organic Synthesis, 3rd. Ed. (John Wiley & Sons, N.Y. (1999)). The ester is decomposed by using a conventional procedure which does not affect another portion of the molecule.

Whereafter, for any of the above procedures, when a pharmaceutically acceptable salt of a compound of Formula I is required, it is obtained by reacting the acid of Formula I with a physiologically acceptable base or by reacting a basic compound of Formula I with a physiologically acceptable acid or by any other conventional procedure.

The term "$C_1$-$C_{10}$ alkyl" represents a straight, branched, or cyclic alkyl chain having from one to ten carbon atoms.

The term "$C_2$-$C_{10}$ alkenyl" represents straight or branched unsaturated alkyl chains having from two to ten carbon atoms, and having one or more carbon-carbon double bond, such as, dienes and trienes. This group also includes both E and Z isomers.

The term "aryl" represents groups such as phenyl, substituted phenyl, and naphthyl. The term "arylalkyl" represents a $C_1$-$C_4$ alkyl group bearing one or more aryl groups.

The term "affecting" refers to a formula I compound acting as an agonist at an excitatory amino acid receptor. The term "excitatory amino acid receptor" refers to a metabotropic glutamate receptor, a receptor that is coupled to cellular effectors via GTP-binding proteins. The term "cAMP-linked metabotropic glutamate receptor" refers to a metabotropic receptor that is coupled to inhibition of adenylate cyclase activity.

The term "neurological disorder" refers to both acute and chronic neurodegenerative conditions, including cerebral deficits subsequent to cardiac bypass surgery and grafting, cerebral ischemia (for example stroke resulting from cardiac arrest), spinal cord trauma, head trauma, Alzheimer's Disease, Huntington's Chorea, amyotrophic lateral sclerosis, AIDS-induced dementia, perinatal hypoxia, hypoglycemic neuronal damage, ocular damage and retinopathy, cognitive disorders, idiopathic and drug-induced Parkinson's Disease. This term also includes other neurological conditions that are caused by glutamate dysfunction, including muscular spasms, migraine headaches, urinary incontinence, drug tolerance, withdrawal, and cessation (i.e. opiates, benzodiazepines, nicotine, cocaine, or ethanol), smoking cessation, emesis, brain edema, chronic pain, sleep disorders, convulsions, Tourette's syndrome, attention deficit disorder, and tardive dyskinesia.

The term "psychiatric disorder" refers to both acute and chronic psychiatric conditions, including schizophrenia, anxiety and related disorders (e.g. panic attack and stress-related cardiovascular disorders), depression, bipolar disorders, psychosis, and obsessive compulsive disorders.

A particular aspect of the present invention includes a method for affecting the cAMP-linked metabotropic glutamate receptors in a patient, which comprises administering to a patient requiring modulated excitatory amino acid neurotransmission a pharmaceutically-effective amount of a compound of formula I.

Another particular aspect of the present invention includes a method of administering an effective amount of a compound of formula II, where $R^{13}$ and $R^{14}$ are both hydrogen (a di-acid), which comprises administering to a patient requiring modulated excitatory amino acid neurotransmission a pharmaceutically effective amount of a compound of formula I.

Another particular aspect of the present invention includes a method for treating a psychiatric disorder in a patient which comprises administering to the patient in need of treatment thereof a pharmaceutically-effective amount of a compound of formula I.

Another particular aspect of the present invention includes a method for treating a neurological disorder in a patient which comprises administering to the patient in need of treatment thereof a pharmaceutically-effective amount of a compound of formula I.

A preferred method for treating a psychiatric disorder in a patient comprises administering to the patient in need thereof a pharmaceutically-effective amount of a compound of formula I wherein said psychiatric disorder is schizophrenia, anxiety and related disorders, depression, dipolar disorders, psychosis, and obsessive compulsive disorders.

A preferred method for treating a neurological disorder in a patient comprises administering to the patient in need thereof a pharmaceutically-effective amount of a compound of formula I wherein said neurological disorder is cerebral deficits subsequent to cardiac bypass and grafting; cerebral ischemia; spinal cord trauma; head trauma; Alzheimer's Disease; Huntington's Chorea; amyotrophic lateral sclerosis; AIDS-induced dementia; perinatal hypoxia; hypoglycemic neuronal damage; ocular damage and retinopathy; cognitive disorders; idiopathic and drug-induced Parkinsons' Disease; muscular spasms; migraine headaches; urinary incontinence; drug tolerance, withdrawal, and cessation; smoking cessation; emesis; brain edema; chronic pain; sleep disorders; convulsions; Tourette's syndrome; attention deficit disorder; and tardive dyskinesia.

A more preferred method for treating a psychiatric disorder in a patient comprises administering to the patient in need thereof a pharmaceutically-effective amount of a compound of formula I wherein said psychiatric disorder is anxiety and related disorders.

A more preferred method for treating a neurological disorder in a patient comprises administering to the patient in need thereof a pharmaceutically-effective amount of a compound of formula I wherein said neurological disorder is drug tolerance, withdrawal, and cessation; or smoking cessation.

An additional aspect of the present invention is a compound of formula I, or a pharmaceutically acceptable salt thereof, for use as a pharmaceutical.

Another aspect of the present invention includes the use of a compound of formula I, or a pharmaceutically acceptable salt thereof, for the manufacture of a medicament for treating neurological or psychiatric disorders.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. For example, a typical daily dose may contain from about 25 mg to about 300 mg of the active ingredient. The compounds can be administered by a variety of routes including oral, rectal, transdermal, subcutaneous, intravenous, intramuscular, bucal or intranasal routes. Alternatively, the compound may be administered by continuous infusion.

As used herein the term "patient" refers to a mammal, such as a mouse, guinea pig, rat, dog or human. It is understood that the preferred patient is a human.

The term "treating" (or "treat") as used herein includes its generally accepted meaning which encompasses prohibiting, preventing, restraining, and slowing, stopping, or reversing progression of a resultant symptom. As such, the methods of this invention encompass both therapeutic and prophylactic administration.

If not commercially available, the necessary starting materials for the above procedures may be made by procedures which are selected from standard techniques of organic and heterocyclic chemistry, techniques which analogous to the syntheses of known, structurally similar compounds, and the procedures described in the Examples, including novel procedures.

A further aspect of the present invention provides for a method of administering an effective amount of a compound of formula II, where $R^{13}$ and $R^{14}$ are both hydrogen (a di-acid), which comprises administering to a patient requiring modulated excitatory amino acid neurotransmission a pharmaceutically-effective amount of a compound of formula I.

Compounds of formula I are converted via enzymatic or hydrolytic process in vivo, to form compounds of formula II, where $R^{13}$ and $R^{14}$ are both hydrogen (a di-acid), as shown in Scheme 1 below.

Scheme 1: In Vivo Conversion

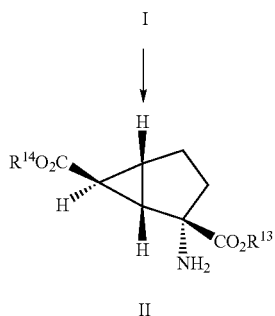

In particular, a crystalline form of a compound of formula I may be prepared according to the route outlined in Scheme 2 below in which each of $R^{13}$ and $R^{14}$, respectively, represents a value defined for the groups $R^{13}$ and $R^{14}$. The process described in Scheme 2 is a synthesis method for the preparation of a crystalline hydrochloride salt form of a compound of formula I and a methanesulfonate salt form of a compound of formula I.

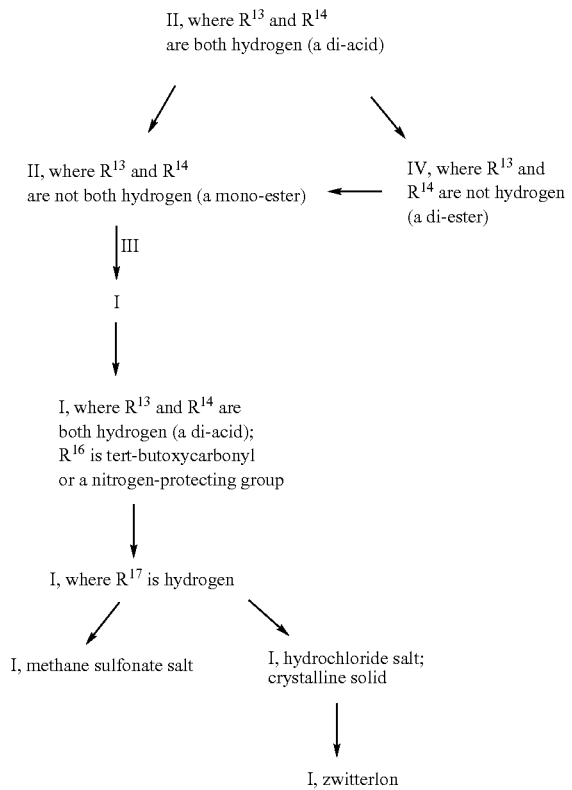

In scheme 2 above, the monohydrate of II, where $R^{13}$ and $R^{14}$ are both hydrogen (a di-acid), is treated with thionyl chloride and methanol affording the corresponding di-ester of II. Alternatively, catalytic hydrochloric acid may be used in place of thionylchloride. The di-ester, formula II, is amidated with a compound of formula III using dicyclohexylcarbodiimide (DCC), 1-(3-dimethylaminopropyl)-3-ethylcarbodiimide (EDCI) or isobutyl chloroformate as a coupling agent to afford a di-ester protected peptidyl compound of formula I. This transformation could also be achieved using the acid chloride or by using a variety of other peptide coupling reagents, for example, diphenyl chlorophosphate and 2-chloro-4,6-dimethoxy-1,3,5-triazine (CDMT), bis(2-oxo-3-oxazolidinyl)phosphinic chloride and benzotriazol-1-yloxytris(dimethylamino)phosphonium hexafluorophosphate.

The hydrolysis of the di-ester protected peptidyl compound of formula I with a suitable base such as lithium hydroxide or sodium hydroxide in THF affords the di-acid protected peptidyl compound of formula I, where R13 and R14 are both hydrogen (a di-acid). The di-acid protected peptidyl compound of formula I may be deprotected with a mineral or organic acid in a suitable solvent. Such conditions may produce the corresponding acid salt of the di-acid peptidyl compound of formula I as an amorphous solid or, directly, a crystalline solid. In the case of an amorphous solid, subsequent crystallization may occur from suitable solvents. For example, a di-acid protected peptidyl compound of formula I when treated hydrogen chloride gas in ethyl acetate provides the deprotected hydrochloride salt as an amorphous solid. The amorphous hydrochloride compound may then be crystallized from acetone and water to afford the crystalline hydrochloride salt compound of formula I. In the case of a crystalline solid which is formed directly, filtration of the reaction mixture may afford the crystalline salt. The zwitterionic compound of formula I is afforded by treatment of the crystalline hydrochloride salt of formula I with sodium hydroxide. It will be appreciated by one of ordinary skill in the art that a compound of formula I may be prepared in one procedure where the indicated intermediates are not isolated.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.*, 1996, 35, 1661-1672 and 1997, 36, 1-11).

The ability of formula I compounds to treat anxiety or a related disorder may be demonstrated using the well known fear potentiated startle and elevated plus maze models of anxiety described respectively in Davis, Psychopharmacology, 62:1; 1979 and Lister, Psychopharmacol, 92:180-185; 1987.

In Vitro Receptor Binding

To study the ability to affect receptor binding of compounds of the present invention in comparison to LY354740, displacement of a high affinity mGluR2 antagonist radioligand [$^3$H]LY341495 to cell membranes from human mGluR2, human mGluR3, and native rat brain tissues was determined. (See, Ornstein P. L., Arnold M. B., Bleisch T. J., Wright R. A., Wheeler W. J., and Schoepp D. D., [$^3$H] LY341495, a highly potent, selective and novel radioligand for labeling group II metabotropic receptors. *Bioorg. Med. Chem. Lett.* 8: 1919-1922 (1998); and Johnson B. G., Wright R. A., Arnold M. B., Wheeler W. J., Ornstein P. L., and Schoepp D. D., [$^3$H]LY341495 as a novel rapid filtration antagonist radioligand for group II metabotropic receptors:

Characterization of binding to membranes of mGlu receptor subtype expressing cells. *Neuropharmacology* 38: 1519-1529 (1999))

As shown in Table 1 below, LY354740 displaced [$^3$H] LY341495 binding to rat forebrain membranes with a potency similar to that observed in human recombinant receptors. In contrast, the compound of formula I did not appreciably displace [$^3$H]LY341495 binding to rat forebrain membranes at up to 10,000 nM.

TABLE 1

Comparison of receptor binding of compounds of the present invention with LY354740

| Receptor Preparation | Displacement of $^3$H-LY341495 binding (Ki, nM) (mean ± S.E., N = 3) | |
| --- | --- | --- |
| | LY354740 | Formula I |
| Human mGluR2 | 84.7 ± 11.1 | >10,000 |
| Human mGluR3 | 125.6 ± 4.8 | >10,000 |
| Rat Forebrain | 80.0 ± 7.3 | >10,000 |

In Vivo Actions in Rat Fear Potentiated Startle Anxiety Model

To study the oral potencies of compounds of the present invention in comparison to LY354740 in an mGlu2/3 receptor linked therapeutic animal model, studies in the rat, fear-potentiated startle assay were performed. This model was specifically chosen, as it is highly sensitive to mGlu2/3 agonists such as LY354740 and compounds of the present invention. (See, Helton D. R., Tizzano J. P., Monn J. A., Schoepp D. D., and Kallman M. J., Anxiolytic and side-effect profile of LY354740: A potent, high selective, orally active agonist for group II metabotropic glutamate receptors, *J. Pharmacol. Exp. Ther.* 284: 651-660 (1998)). To verify that the actions of a compound of formula I in this model were mGlu2/3 receptor mediated, as has been shown previously for LY354740 (See, Tizzano, J. P., Griffey K. I., Ornstein P. L., Monn J. A., and Schoepp D. D., Actions of mGlu receptor agonists on fear-conditioning versus fear-expression in rats, *Neuropharmacology,* 38:A45 (#144) (1999)), the ability of LY341495 (an mGlu2/3 receptor antagonist) (See, Kingston A. E., Ornstein P. L., Wright R. A., Johnson B. G., Mayne N. G., Burnett J. P., Belagaje R., Wu S., and Schoepp D. D., LY341495 is a nanomolar potent and selective antagonist for group II metabotropic glutamate receptors, *Neuropharmacology,* 37: 1-12 (1998)) to block compound-mediated suppression of fear-potentiated startle was also determined. As a positive control in each experiment, diazepam (0.6 mg/kg i.p.) was used. All experiments were performed in fed rats.

In the fear potentiated startle model, animals are exposed to a neutral stimulus such as light (conditioned stimulus) with an aversive stimulus such as a shock (unconditioned stimulus). Following conditioning, when the animals are presented with a loud acoustic stimulus, larger startle responses are elicited when the startle stimulus is preceded by light.

Diazepam and buspirone hydrochloride, which are clinically proven anxiolytics, are effective at reducing the fear (increased startle response) associated with the presentation of light in the fear potentiated startle model, and in reducing the fear of open spaces in the elevated plus maze model.

Male Long Evans rats (180-400 g) or male NIH Swiss mice (18-35 g) were obtained from Harlan Sprague-Dawley, Cumberland, Ind., USA and acclimated at least 3 days before testing. Animals were housed at 23±2° C. (relative humidity 30% to 70%) and given Purina Certified Rodent Chow and water ad libitum. The photoperiod was 12 hours of light and 12 hours of dark, with dark onset at approximately 1800 hours.

Test compounds were dissolved in a vehicle of purified water and neutralized with 5 N NaOH to a pH of 7-8 when applicable. Diazepam (Sigma Chemical Company, St. Louis, Mo.) was suspended in purified water by the drop-wise addition of Tween 80. Control animals received the respective vehicle.

SL-LAB (San Diego Instruments, San Diego, Calif.) chambers were used for conditioning sessions and for the production and recording of startle responses. A classical conditioning procedure was used to produce potentiation of startle responses. Briefly, on the first 2 days, rats were placed into dark startle chambers in which shock grids were installed. Following a 5-minute acclimation period, each rat received a 1 mA electric shock (500 ms) preceded by a 5 second presentation of light (15 watt) which remained on for the duration of the shock. Ten presentations of the light and shock were given in each conditioning session, rats were gavaged with a solution of test compound of water and startle testing sessions were conducted. A block of 10 consecutive presentations of acoustic startle stimuli (110 dB, non-light-paired) were presented at the beginning of the session in order to minimize the influences of the initial rapid phase of habituation to the stimulus. This was followed by 20 alternating trials of the noise alone or noise preceded by the light. Excluding the initial trial block, startle response amplitudes for each trial type (noise-alone vs. light+noise) were averaged for each rat across the entire test session.

As shown in the first row of Table 2, below, when given orally to fed rats, compounds of the present invention were active in the rat fear-potentiated startle test at 300 times lower doses when compared to LY354740. If this in vivo animal model data directly predicts human anxiety responses, compounds of the present invention would produce anxiolytic effects in humans at 300 fold lower doses than the parent compound. Furthermore, the ability to produce a longer duration at lower doses when compared to parent may allow for once-a day dosing, as opposed to twice a day dosing.

In Vivo Exposure as Measured by Rat Plasma Concentration

To study the in vivo exposure of LY354740 following oral dosing of compounds of the present invention in comparison to LY354740, studies measuring the plasma concentrations of LY354740 in rats were performed.

Mature Fischer 344 male rats (190-270 gram) were obtained from Harlan Sprague-Dawley, Cumberland, Ind., USA and acclimated in the study housing for 3 days. On day 4, test compounds were dissolved in buffered water (1 mg/ml=test compound/20 mM potassium dihydrogen phosphate, pH=2) and given orally as a single 5 mg/kg dose. Blood samples were collected through orbital sinus or cardiac puncture (last time point) at 0.5 and 1 hour or, alternatively, 1 and 3 hours. Plasma samples were stored at −20° C. in the presence of phenylmethylsulfonyl fluoride, a protease inhibitor, prior to analysis. Plasma samples and internal standard compounds were pretreated by solid phase extraction (SAX support, methanol/water/dilute acetic acid). As shown in the second row of Table 2, below, the plasma concentrations (ng/ml) of LY354740 for each test compound were determined by LC/MS/MS and are presented as a sum of the concentrations at the 0.5 and 1 hour or, alternatively, 1 and 3 hour sample time points.

TABLE 2

Comparison LY354740 and compounds of the present invention in the rat fear-potentiated startle assay

| Parameter Measured | Compound | |
| --- | --- | --- |
| | LY354740 | formula I |
| MED (1 hour pre-treatement) | 3.0 mg/kg p.o. | 0.01 mg/kg p.o. |
| Rat Exposure (ng/ml of LY354740 following 5 mg/kg p.o.) | 466 ng/ml | 7114 ng/ml |

As shown above in Tables 1 and 2, in vitro studies show that the compounds of the present invention had no appreciable affinity per se for mGlu2/3 receptors. This indicates that the in vivo pharmacology of this compound in rats and humans would likely reflect the conversion of the prodrug to the parent molecule, LY354740, which then acts at mGlu2/3 receptors to produce a therapeutic effect. Further, in fact, when given orally to rats, the compounds of the current invention exhibit a 15 fold increase in plasma concentration of LY354740 when compared to LY354740. This demonstrates compounds of the present invention are converted to LY354740 in vivo.

The compounds of the present invention are preferably formulated prior to administration. Therefore, another aspect of the present invention is a pharmaceutical formulation comprising a compound of formula I, or a pharmaceutically acceptable salt thereof, and a pharmaceutically-acceptable carrier, diluent, or excipient. The pharmaceutical formulations may be prepared by procedures well-known by one of ordinary skill in the art. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg active ingredient, preferably about 25 mg to about 300 mg active ingredient. As used herein the term "active ingredient" refers to a compound included within the scope of formula I.

The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use. Proton nuclear magnetic resonance ($^1$H NMR) spectra were obtained on a Bruker Avance II bay-500 at 500 MHz, a Bruker Avance I bay-200 at 200 MHz or a Varian Inova at 500 MHz. Electrospray mass spectroscopy (ESI) was performed on a Agilent MSD/B intrument using acetonitrile/aqueous ammonium acetate as the mobile phase. Free atom bombardment mass spectroscopy (FABMS) was performed on a VG ZAB-2SE instrument. Field desorption mass spectroscopy (FDMS) was performed using either a VG 70SE or a Varian MAT 731 instrument. Optical rotations were measured with a Perkin-Elmer 241 polarimeter. Chromatographic separation on a Waters Prep 500 LC was generally carried out using a linear gradient of the solvents indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography was performed as described by Still, et al. Still, Kahn, and Mitra, *J. Org. Chem.*, 43, 2923 (1978). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Gallenkamp hot air bath melting point apparatus or a Büchi melting point apparatus, and are uncorrected.

The abbreviations, symbols and terms used in the examples have the following meanings.

Ac=acetyl
Anal.=elemental analysis
Bn or Bzl=benzyl
Bu=butyl
BOC=butoxycarbonyl
calcd=calculated
$D_2O$=deuterium oxide
DCC=dicyclohexylcarbodiimide
DIBAL-H=diisobutyl aluminum hydride
DMAP=dimethylaminopyridine
DMF=dimethylformamide
DMSO=dimethylsulfoxide
EDC=N-ethyl-N'N'-dimethylaminopropyl carbodiimide
Et=ethyl
EtOH=ethanol FAB=Fast Atom Bombardment (Mass Spectrascopy)
FDMS=field desorption mass spectrum
HOAt=1-hydroxy-7-azabenzotriazole
HOBt=1-hydroxybenzotriazole
HPLC=High Performance Liquid Chromatography
HRMS=high resolution mass spectrum
i-PrOH=isopropanol
IR=Infrared Spectrum
L=liter
Me=methyl
MeOH=methanol
MPLC=Medium Pressure Liquid Chromatography
Mp=melting point
MTBE=t-butyl methyl ether NBS=N-bromosuccinimide
NMR=Nuclear Magnetic Resonance
Ph=phenyl
p.o.=oral administration
i-Pr=isopropyl
Rochelle's Salt=potassium sodium tartrate
SM=starting material
TBS=tert-butyldimethylsilyl
TEA=triethylamine
Temp.=temperature
TFA=trifluoroacetic acid
THF=tetrahydrofuran
TLC=thin layer chromatography
t-BOC=tert-butoxycarbonyl

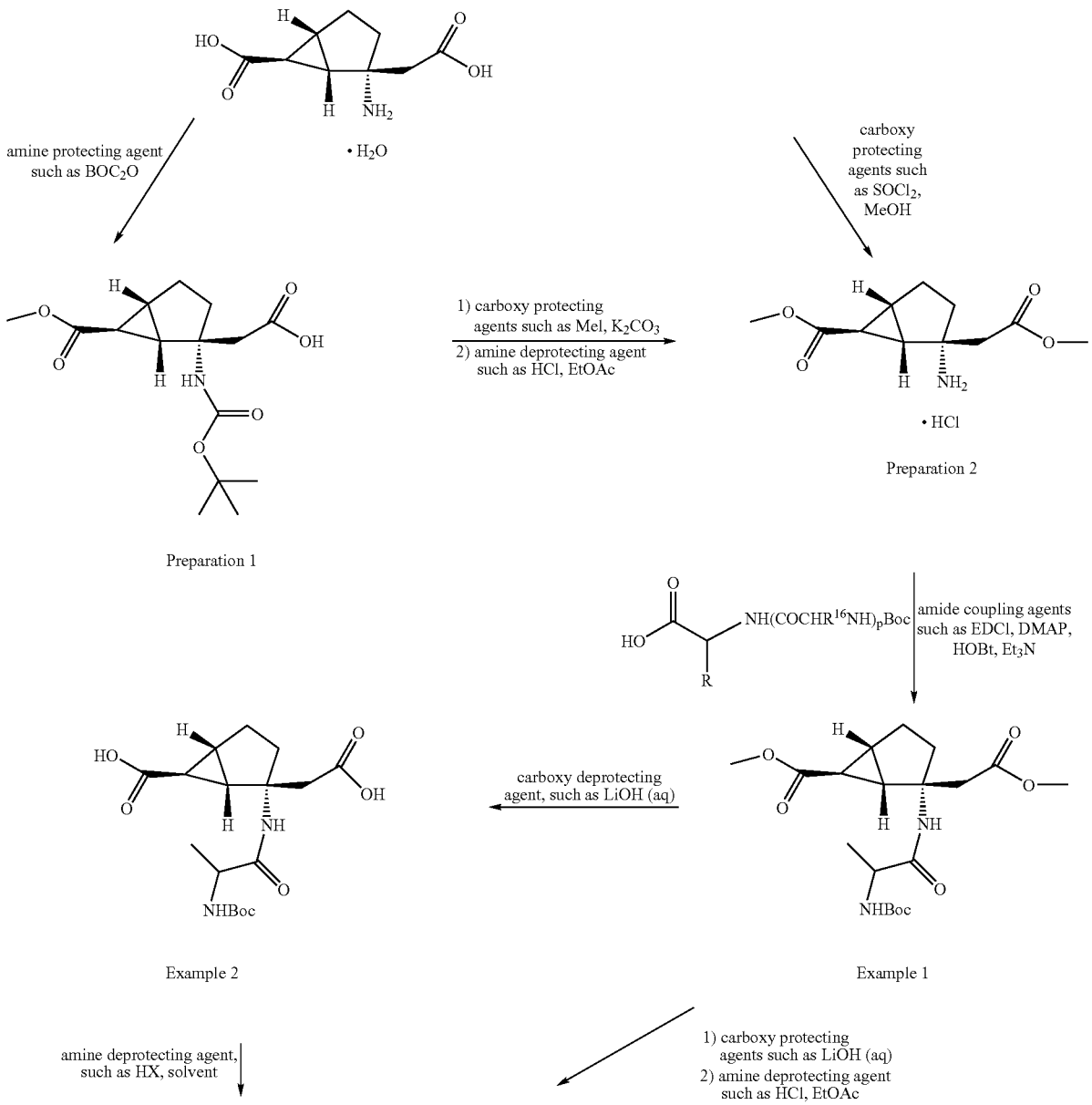

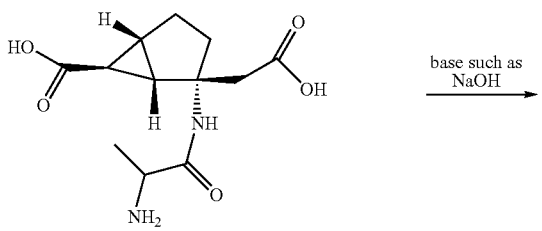 base such as NaOH → 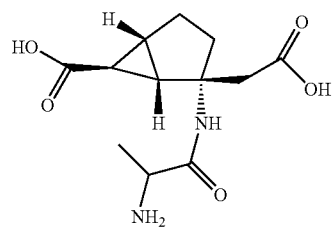

Example 3 (X = Cl)
Example 4 (X = OSO₂Me)

Example 5

Preparation 1

Synthesis of (1S,2S,5R,6S)-2-tert-Butoxycarbonylamino-bicyclo[3.1.0]hexane-2,6-dicarboxylic acid

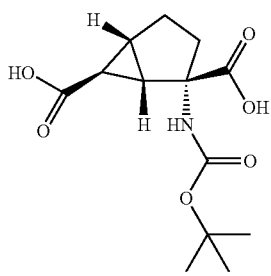

A 1 L flask was charged with (1S,2S,5R,6S)-2-amino-bicyclo[3.1.0]hexane-2,6-dicarboxylic acid monohydrate (24.4 g, 0.12 mol, 1 equiv), dioxane (200 mL) and di-tert-butyl dicarbonate (52.4 g, 0.24 mol, 2.0 equiv). The suspension was vigorously stirred while 1N sodium hydroxide (420 mL, 3.5 equiv) was added. The mixture was stirred for 2 days, then 2.0 more equiv of di-tert-butyl dicarbonate were added and the reaction stirred for 3 additional days at room temperature. After 5 total days of reaction, water (400 mL) was added to dissolve the salts. The aqueous layer was extracted with ethyl acetate (4×100 mL) and acidified to pH 2 with 6 N hydrochloric acid. The acidic aqueous phase was extracted with ethyl ether (6×200 mL). The combined ether extracts were washed with water (250 mL) and brine (250 mL). After drying over sodium sulfate, solvents were evaporated under vacuum to afford a foamy white solid (26.4 g).

77% Yield; mp 100-101° C. $[\alpha]_D^{25}$=−41.1° (c=1.0, MeOH). $^1$H NMR (Methanol-$d_4$) δ: 4.98 (brs, 1H), 2.44 (dd, 1H, J=6.2, 2.6 Hz), 2.19-1.92 (m, 4H), 1.62 (t, 1H, J=2.8 Hz), 1.43 (s, 9H), 1.29 (m, 1H). $^{13}$C NMR (Methanol-$d_4$) δ: 175.6, 175.2, 158.2, 60.1, 34.6, 31.9, 28.4, 27.2, 25.6, 20.6. MS (Electrospray): 285.12.

Preparation 2

Synthesis of (1S,2S,5R,6S)-2-Amino-bicyclo[3.1.0]hexane-2,6-dicarboxylic acid dimethyl ester hydrochloride

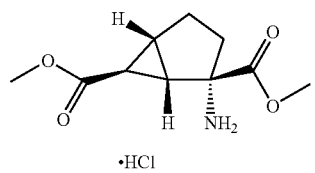
·HCl (1S,2S,5R,6S)-2-tert-Butoxycarbonylamino-bicyclo[3.1.0]hexane-2,6-dicarboxylic acid (20 g, 0.07 mol, 1.0 equiv) was dissolved in 210 ml of dry dimethylformamide and potassium carbonate (21.3 g, 0.154 mol, 2.2 equiv) was added at 0° C. under nitrogen. After 15 minutes, methyl iodide (17.6 ml, 0.28 mol, 4.0 equiv) was added. The reaction mixture was warmed up slowly and stirred at room temperature for 3 h. Water (200 ml) was added and the aqueous phase was extracted with ethyl ether (4×75 ml each). The combined organic phase was washed with cold water (4×50 ml), and the aqueous phase extracted again with ethyl ether (2×50 ml). After drying the organic phase over sodium sulfate and evaporating under vacuum, a foamy solid ((1S,2S,5R,6S)-2-tert-butoxycarbonylamino-bicyclo[3.1.0]hexane-2,6-dicarboxylic acid-2,6-dimethyl ester) was obtained (19.2 g, 87% yield).

This compound was diluted with 150 ml of a saturated solution of hydrogen chloride gas in ethyl acetate and the mixture vigorously stirred for 1 hour (a white precipitate appeared within 15 minutes). The solid was filtered, rinsed with ethyl ether and thoroughly dried under high vacuum.

73% Yield; mp 193-194° C. $[\alpha]_D^{25}$=+22.2° (c=1.0, MeOH). $^1$H NMR (D$_2$O) δ: 3.86 (s, 3H), 3.67 (s, 3H), 2.31-2.04 (m, 6H), 1.57 (m, 1H). $^{13}$C NMR (Methanol-$d_4$) δ: 171.9, 170.2, 65.6, 52.8, 51.2, 32.4, 29.9, 28.5, 26.2, 20.7.

Alternative Synthesis of (1S,2S,5R,6S)-2-Amino-bicyclo[3.1.0]hexane-2,6-dicarboxylic acid dimethyl ester hydrochloride

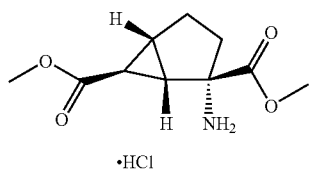
·HCl

Thionyl chloride (807 mL, 11.1 mol) was added to methanol (9.5 L) over a period of 1 h while maintaining the temperature between 2-20° C. The solution was maintained for 30 min, then (1S,2S,5R,6S)-2-amino-bicyclo[3.1.0]hexane-2,6-dicarboxylic acid monohydrate (1.61 kg, 7.92 mol) was added. The resulting solution was heated to 47° C. and maintained between 47-50 □C for 17 h. Approximately 7.3 L of methanol was then removed by vacuum distillation (47-50° C., 240-275 mm Hg). The remaining methanol was removed by azeotropic distillation with t-butyl methyl ether (MTBE) at atmospheric pressure [added MTBE (10 L), removed 8.5 L; added MTBE (10 L), removed 8.5 L; added MTBE (8 L), removed 5.1 L]. During the course of the distillations a white solid began to precipitate from the solution. After completion of the distillations, MTBE (2 L)

was added to the resulting slurry, and the slurry was cooled to 22° C. The solid was filtered, rinsed with MTBE (2 L) and dried under vacuum to afford 1.94 kg (98%) of the title compound as a white solid.

Analysis Calculated for $C_{10}H_{16}NO_4Cl$: C, 48.10; H, 6.46; N, 5.61; Cl, 14.20. Found: C, 47.88; H, 6.25; N, 5.57; Cl, 14.52.

General Procedure for the Coupling Reaction of (1S,2S,5R,6S)-2-Amino-bicyclo[3.1.0]hexane-2,6-dicarboxylic acid dimethyl ester hydrochloride with N-BOC-(L)-aminoacids The starting dimethyl ester hydrochloride salt (1.0 equiv), the product of Example Preparation 2, was suspended in dry dichloromethane (0.1 M solution) under nitrogen. The corresponding N-BOC-aminoacid (1.5 equiv), N-ethyl-N',N'-dimethylaminopropylcarbodiimide (EDC, 1.5 equiv) and 1-hydroxybenzotriazole (HOBt, 1.5 equiv) were added in one portion, followed by triethyl amine(1.0 equiv) via syringe and, finally, dimethylaminopyridine (DMAP, 0.1 equiv). The reaction mixture was stirred overnight at room temperature, then hydrolyzed by addition of 1N hydrochloric acid (20 ml/mmol) and diluted with methylene chloride (10 ml/mmol). The aqueous layer was extracted with methylene chloride (5 ml/mmol) and the combined organic layers washed twice with 1 N hydrochloric acid (10 ml/mmol), and finally with water and brine (10 ml/mmol each). After drying over sodium sulfate and evaporation under vacuum the crude residue was purified by silica gel chromatography using the appropriate eluent (typically mixtures hexanes/ethyl acetate).

Alternative Procedure for the Coupling Reaction of (1S,2S,5R,6S)-2-Amino-bicyclo[3.1.0]hexane-2,6-dicarboxylic acid dimethyl ester hydrochloride with N-BOC-aminoacids A solution of dicyclohexylcarbodiimide (DCC) (1.1 equiv) in methylene chloride (4.0 M solution) was added to a mixture of Preparation 2 (1.0 equiv), triethylamine (1.0 equiv) and N-t-butoxycarbonyl-L-alanine (1.1 equiv) in methylene chloride (1.0 M solution) over a period of approximately 1.5 h while stirring. The resulting mixture was stirred for 1-12 h then filtered. The filter cake (dicyclohexylurea) was rinsed with methylene chloride, and the filtrate was washed with 0.1 M NaHCO₃ followed by 1.0 N hydrochloric acid. The organic phase was dried (Na₂SO₄), filtered and concentrated to afford the title compound as an oil.

EXAMPLE 1

Synthesis of (1S,2S,5R,6S)-2-[(2'S)-(2'-tert-Butoxycarbonylamino)-propionyl]amino-bicyclo[3.1.0]hexane-2,6-dicarboxylic acid dimethyl ester

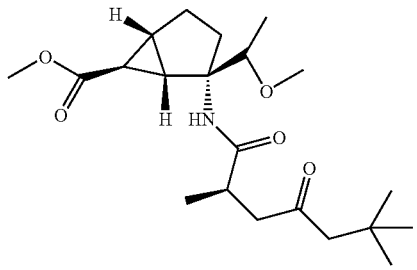

The starting dimethyl ester hydrochloride salt (1.0 equiv), the product of Preparation 2, was suspended in dry dichloromethane (0.1 M solution) under nitrogen. N-BOC-(L)-alanine (1.5 equiv), N-ethyl-N',N'-dimethylaminopropylcarbodiimide (EDC, 1.5 equiv) and 1-hydroxybenzotriazole (HOBt, 1.5 equiv) were added in one portion, followed by triethyl amine(1.0 equiv) via syringe and, finally, dimethylaminopyridine (DMAP, 0.1 equiv). The reaction mixture was stirred overnight at room temperature, then hydrolyzed by addition of 1N hydrochloric acid (20 ml/mmol) and diluted with methylene chloride (10 ml/mmol). The aqueous layer was extracted with methylene chloride (5 ml/mmol) and the combined organic layers washed twice with 1 N hydrochloric acid (10 ml/mmol), and finally with water and brine (10 ml/mmol each). After drying over sodium sulfate and evaporation under vacuum the crude residue was purified by silica gel chromatography using mixtures of hexanes/ethyl acetate.

50% Yield. Foamy white solid. mp 51-52° C. $[\alpha]_D^{25}=-27.7$ (c=0.52, $CHCl_3$) $^1H$ NMR ($CDCl_3$) δ: 7.28 (brs, 1H), 5.04 (brd, 1H, J=7.6 Hz), 4.16 (m, 1H), 3.74 (s, 3H), 3.66 (s, 3H), 2.49 (dd, 1H, J=13.9, 8.3 Hz), 2.42 (dd, 1H, J=6.3, 2.8 Hz), 2.18-1.89 (m, 3H), 1.70 (t, 1H, J=2.9 Hz), 1.45 (s, 9H), 1.33 (d, 3H, J=7.0 Hz), 1.19 (m, 1H). $^{13}C$ NMR ($CDCl_3$) δ: 172.8, 172.6, 172.6, 155.7, 80.2, 66.3, 52.6, 51.8, 49.5, 34.4, 32.0, 28.2, 28.1, 26.6, 21.1, 17.6.

Alternative Synthesis of (1S,2S,5R,6S)-2-[(2'S)-(2'-tert-Butoxycarbonylamino)-propionyl]amino-bicyclo[3.1.0]hexane-2,6-dicarboxylic acid dimethyl ester A solution of dicyclohexylcarbodiimide (DCC) (1.1 equiv) in methylene chloride (4.0 M solution) was added to a mixture of Example Preparation 2 (1.0 equiv), triethylamine (1.0 equiv) and N-t-butoxycarbonyl-L-alanine (1.1 equiv) in methylene chloride (1.0 M solution) over a period of approximately 1.5 h while stirring. The resulting mixture was stirred for 1-12 h then filtered. The filter cake (dicyclohexylurea) was rinsed with methlyene chloride, and the filtrate was washed with 0.1 M NaHCO₃ followed by 1.0 N hydrochloric acid. The organic phase was dried (Na₂SO₄), filtered and concentrated to afford the title compound as an oil.

EXAMPLE 2

Synthesis of (1S,2S,5R,6S)-2-[(2'S)-(2'-tert-Butoxycarbonylamino)-propionyl]amino-bicyclo[3.1.0]hexane-2,6-dicarboxylic acid

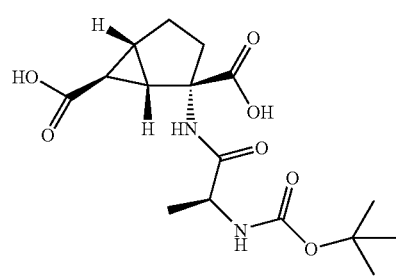

A solution of 2 M NaOH (5.45 L, 10.9 mol) was added to a solution of (1S,2S,5R,6S)-2-[(2'S)-(2'-tert-butoxycarbonylamino)-propionyl]amino-bicyclo[3.1.0]hexane-2,6-dicarboxylic acid dimethyl ester (4.52 mol, crude) in THF (2.8 L). The resulting mixture was stirred at ambient temperature for 3 h then extracted with $CH_2Cl_2$ (2×3 L). Ethyl acetate (5 L) and tetrahydrofuran (3 L) were then added to the aqueous phase. While stirring, concentrated HCl (970 mL) was added to the mixture until the pH=2. The organic phase was dried ($MgSO_4$) and filtered. The aqueous phase was then extracted with ethyl acetate (5 L). The organic phase was dried ($MgSO_4$), filtered and combined with the previous organic phase. The combined organics were concentrated to a soft solid. Ethyl acetate was then added, and the mixture was concentrated to a soft solid. Ethyl acetate (3.5 L) was again added. The mixture was concentrated until a freely flowing suspension was present. Heptane (1.8 L) was then added, and the slurry was stirred at ambient temperature for 15 h. The solid was filtered, washed with heptane (3 L) then dried under vacuum to afford the title compound.

Yield 1.36 kg (84%) as an approximate 85:15 mixture of rotamers as a white solid. $[\alpha]_D$ 25-24.8(C1.0, MeOH) $^1$H NMR (DMSO-$d_6$) δ 12.20 (s, 2H), 8.40 (s, 0.85H), 8.36 (s, 0.15H), 6.69 (d, J=8.2 Hz, 0.85H), 6.33 (br d, 0.15H), 3.99 (quintet, J=7.2 Hz, 0.85H), 3.84 (br m, 0.15H), 2.18-2.13 (m, 2H), 1.91-1.84 (m, 1H), 1.82-1.75 (m, 2H), 1.46 (br s, 0.85H), 1.43 (br s, 0.15H), 1.35 (s, 9H), 1.23-1.15 (m, 1H), 1.13 (d, J=6.9 Hz, 3H). $^{13}$C NMR ($CD_3OD$) δ 176.4, 176.0 (2 C), 157.5, 80.5, 67.3 (minor rotamer), 67.2 (major rotamer), 50.9, 35.6, 32.8, 29.3, 28.7, 27.4, 22.1, 18.5. MS (EI) calcd for $C_{16}H_{28}N_3O_7$ (M+$NH_4^+$) 374.20, found 374.24 m/z.

Alternative Synthesis of (1S,2S,5R,6S)-2-[(2'S)-(2'-tert-Butoxycarbonylamino)-propionyl]amino-bicyclo[3.1.0]hexane-2,6-dicarboxylic acid

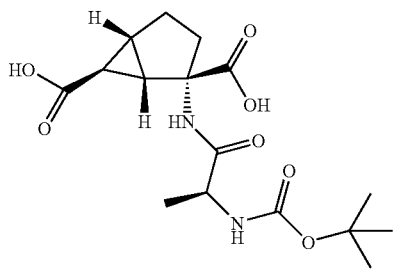

A solution of (1S,2S,5R,6S)-2-amino-bicyclo[3.1.0]hexane-2,6-dicarboxylic acid monohydrate (85 g, 418 mmol) and MeOH (850 mL) was cooled to 10° C. Thionyl chloride (199 g, 1.67 mol) was added at a rate such that the temperature did not exceed 20° C. The solution was then heated to 50° C. and stirred for 6 h. Upon completion of the reaction, the solution was cooled to room temperature and concentrated to approximately 170 mL total volume under reduced pressure at 20-30° C. Water (850 mL) was added, and the pH of the solution was adjusted to approximately pH 2.0 with 1.0 N NaOH (300 mL). The solution was concentrated under reduced pressure until the temperature reached approximately 40° C. Methylene chloride (850 mL) was then added, and the pH of the solution was adjusted to pH 8 with 1.0 N NaOH (180 mL). The phases were separated, and the aqueous phase was extracted with $CH_2Cl_2$ (425 mL). The combined organic phases containing the corresponding dimethyl ester were concentrated to approximately 425 mL total volume and held for further processing.

In a separate reaction vessel a solution of N-t-butoxycarbonyl-L-alanine (83.2 g, 439 mmol) and 4-methylmorpholine (44.4 g, 439 mmol) in $CH_2Cl_2$ (712 mL) was cooled to −5−−10° C. Isobutyl chloroformate (59.9 g, 439 mmol) was then added at rate such that the temperature did not exceed −5° C. Upon completion of the addition, the solution was stirred for 15 min. Simultaneously, $CH_2Cl_2$ (20 mL) was added to the dimethyl ester solution previously prepared, and this solution was cooled to −5° C. The dimethyl ester solution (445 mL) was then added to the isobutyl mixed anhydride mixture. The cooling bath was removed, and the corresponding mixture was stirred for 30 min. A solution of 1.0 N HCl (445 mL) was then added. The phases were separated, and the organic phase was washed with 1.0 N HCl (445 mL). The organic phase was concentrated to approximately 180 mL total volume. THF (450 mL) was then added, and the resulting solution was concentrated to approximately 180 mL total volume. To this solution was added 1.0 N NaOH (1.67 L, 1.67 mol). The resulting mixture was heated to 40° C., stirred for 1.5 h then cooled to room temperature. Ethyl acetate (2.4 L) was added, and the pH of the aqueous phase was adjusted to pH 2.1 with concentrated HCl (150 mL). The phases were separated, and the aqueous phase was extracted with ethyl acetate (800 mL). The combined organic phases were dried with $MgSO_4$, filtered and washed with EtOAc (2×320 mL). The resulting solution was then concentrated to approximately 400 mL total volume. Ethyl acetate (800 mL) was added, and the solution was concentrated to 400 mL). This ethyl acetate addition/concentration was repeated again, then heptane (640 mL) was added. The resulting mixture was stirred for 2 h, filtered and washed with a 2:1 mixture of heptane-ethyl acetate (2×320 mL) to afford 115.5 g (78% yield) of (1S,2S,5R,6S)-2-[(2'S)-(2'-tert-butoxycarbonylamino)-propionyl]amino-bicyclo[3.1.0]hexane-2,6-dicarboxylic acid as a white solid.

EXAMPLE 3

Synthesis of (1S,2S,5R,6S)-2-[(2'S)-(2'-Amino)-propionyl]amino-bicyclo[3.1.0]hexane-2,6-dicarboxylic acid hydrochloride

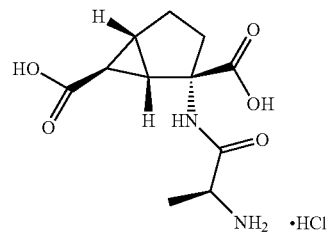

To a solution of ethyl acetate (500 mL) was added HCl (79.0 g, 2.16 mol). The resulting HCl solution was then added to a slurry of (1S,2S,5R,6S)-2-[(2'S)-(2'-tert-butoxycarbonylamino)-propionyl]amino-bicyclo[3.1.0]hexane-2,6-dicarboxylic acid (100 g, 281 mmol) in ethyl acetate (500 mL) at a rate such that the temperature did not exceed 25° C. The resulting mixture was stirred for 3.5 hours then filtered affording 82.6 g of (1S,2S,5R,6S)-2-[(2'S)-(2'-Amino)-propionyl]amino-bicyclo[3.1.0]hexane-2,6-dicarboxylic acid hydrochloride as an amorphous, white solid. This white solid was then added to acetone (290 mL) and water (57 mL). The resulting mixture was heated to 48-52°

C., and water (6.4 mL) was added until all of the solid dissolved. Acetone (2.2 L) was added to the resulting solution over a period of approximately 1 h. When the addition of acetone began, the heating mantle was removed. After the addition was complete, the mixture was cooled to 0--10° C. and stirred for 4 h. The mixture was then filtered and washed with cold acetone (75 mL) affording (1S,2S,5R,6S)-2-[(2'S)-(2'-amino)-propionyl]amino-bicyclo[3.1.0]hexane-2,6-dicarboxylic acid hydrochloride that was dried under vacuum at 40° C. to provide 76.6 g (93% yield) of the title compound as a white, crystalline solid.

72% Yield. White crystalline solid. mp>250° C., dec. $[\alpha]_D^{25}$=−7.80 (c=1.0, MeOH). $^1$H NMR (Methanol-$d_4$) δ: 3.96 (q, 1H, J=7.0 Hz), 2.47 (dd, 1H, J=6.3, 2.7 Hz), 2.37 (dd, 1H, J=13.6, 8.2 Hz), 2.18-1.92 (m, 3H), 1.66 (t, 1H, J=3.0 Hz), 1.53 (d, 3H, J.=7.0 Hz), 1.46-1.34 (m, 1H). $^{13}$C NMR (Methanol-$d_4$) δ: 175.2, 174.7, 170.2, 66.4, 49.0, 36.6, 32.0, 28.5, 26.3, 21.2, 16.6. 80% Yield. White solid.

EXAMPLE 4

Synthesis of (1S,2S,5R,6S)-2-[(2'S)-(2'-Amino)-propionyl]amino-bicyclo[3.1.0]hexane-2,6-dicarboxylic acid methanesulfonate

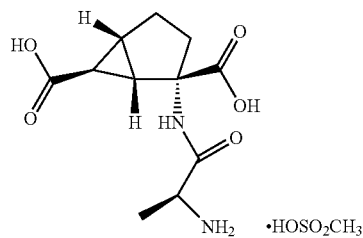

A solution of (1S,2S,5R,6S)-2-[(2'S)-(2'-tert-butoxycarbonylamino)-propionyl]amino-bicyclo[3.1.0]hexane-2,6-dicarboxylic acid (1.07 g, 3.00 mmol), methanesulfonic acid (584 μL, 9.00 mmol) and dioxane (10 mL) was stirred for 48 h. The mixture was filtered and dried to afford (1S,2S,5R,6S)-2-[(2'S)-(2'-Amino)-propionyl]amino-bicyclo[3.1.0]hexane-2,6-dicarboxylic acid methane sulfonate as a crude, white, amorphous solid (1.05 g). A sample of this solid (1.0 g) was dissolved in MeOH (10 mL). The solution was concentrated to 3.3 g total weight and seed crystals were added. Ethyl acetate (10 mL) was then added to the mixture over a period of 15 min. The mixture was stirred for 30 min, filtered and dried under vacuum to afford 830 mg of the title compound as a white, crystalline solid.

Yield 78%. $^1$H NMR (CD$_3$OD) δ 3.96 (q, J=7.1 Hz, 1H), 2.71 (s, 3H), 2.45 (dd, J=6.4, 2.7 Hz, 1H), 2.38 (dd, J=13.9, 8.4 Hz, 1H), 2.20-2.08 (m, 1H), 2.01-1.93 (m, 2H), 1.67 (t, J=2.9 Hz, 1H), 1.52 (d, J=7.0 Hz, 3H), 1.46-1.35 (m, 1H) $^{13}$C NMR (CD$_3$OD) δ 176.3, 175.7, 171.2, 67.4, 50.0, 39.5, 35.7, 33.1, 29.5, 27.4, 22.2, 17.6. Anal. Calcd for $C_{12}H_{20}N_2O_8S$: C, 40.90; H, 5.72; N, 7.95. Found: C, 40.81; H,. 5.69; N, 7.83.

EXAMPLE 5

Synthesis of (1S,2S,5R,6S)-2-[(2'S)-(2'-Amino)-propionyl]amino-bicyclo[3.1.0]hexane-2,6-dicarboxylic acid

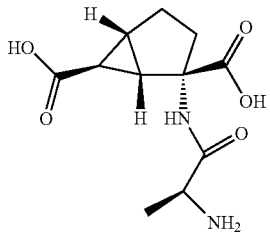

(1S,2S,5R,6S)-2-[(2'S)-(2'-Amino)-propionyl]amino-bicyclo[3.1.0]hexane-2,6-dicarboxylic acid hydrochloride (1.0 g, 3.42 mmol) was dissolved in water (1 mL), and 1.0 N NaOH (3.42 mL, 3.42 mmol) was added. The solution was maintained in the refrigerator for 24 h. The solution remained clear. Acetone (2 mL) was added, and the solution was stored in the refrigerator for 16 h. A white solid precipitated out of solution, and mixture could not be stirred. Acetone (4 mL) was added, and the mixture was stirred at rt, then filtered and dried to afford 630 mg of the title compound as a white crystalline solid which contained 2-4% NaCl.

Yield 72%. $^1$H NMR (CD$_3$OD) δ 3.93 (q, J=7.1 Hz, 1H), 2.48 (dd, , J=6.6, 2.9 Hz, 1H), 2.32 (dd, , J=13.5, 8.4 Hz, 1H), 2.20-2.08 (m, 1H), 2.01-1.90 (m, 2H), 1.61 (t, , J=2.9 Hz, 1H), 1.51 (d, , J=7.0 Hz, 3H), 1.48-1.33 (m, 1H) $^{13}$C NMR (CD$_3$OD) δ 176.9 (2 C), 171.1, 68.0, 50.1, 35.9, 33.2, 29.7, 27.3, 22.5, 17.6.

The invention claimed is:

1. A compound of formula I

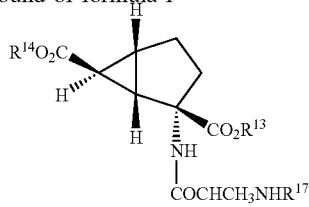

wherein $R^{13}$, $R^{14}$ and $R^{17}$ are hydrogen;

or a pharmaceutically acceptable salt thereof.

2. The pharmaceutically acceptable salt of a compound of formula I as claimed in claim 1 which is (1S,2S,5R,6S)-2-[(2'S)-(2'-Amino)-propionyl]amino-bicyclo[3.1.0]hexane-2,6-dicarboxylic acid hydrochloride salt.

3. The pharmaceutically acceptable salt of a compound of formula I as claimed in claim 1 which is (1S,2S,5R,6S)-2-[(2'S)-(2'-Amino)-propionyl]amino-bicyclo[3.1.0]hexane-2,6-dicarboxylic acid methane sulfonate salt.

4. A pharmaceutical formulation comprising in association with a pharmaceutically acceptable carrier, diluent or excipient, a compound of formula I (or a pharmaceutically acceptable salt thereof) as provided in any one of claims 2 or 3.

5. A compound which is (1S,2S,5R,6S)-2-[2'S)-(2-Amino)-propionyl]amino-bicyclo[3.1.0]hexane-2,6-dicarboxylic acid hydrochloride salt.

* * * * *